US009375279B2

(12) United States Patent
Brannan

(10) Patent No.: US 9,375,279 B2
(45) Date of Patent: Jun. 28, 2016

(54) METHODS OF ADJUSTING AN ABLATION FIELD RADIATING INTO TISSUE USING MICROWAVE FIELD-DETECTING NEEDLE ASSEMBLIES

(71) Applicant: COVIDIEN LP, Mansfield, MA (US)

(72) Inventor: Joseph D. Brannan, Erie, CO (US)

(73) Assignee: Covidien LP, Mansfield, MA (US)

(*) Notice: Subject to any disclaimer, the term of this patent is extended or adjusted under 35 U.S.C. 154(b) by 0 days.

(21) Appl. No.: 14/740,331

(22) Filed: Jun. 16, 2015

(65) Prior Publication Data

US 2015/0272672 A1    Oct. 1, 2015

Related U.S. Application Data

(62) Division of application No. 12/977,390, filed on Dec. 23, 2010, now Pat. No. 9,055,957.

(51) Int. Cl.
*A61B 18/18* (2006.01)
*A61B 18/14* (2006.01)
(Continued)

(52) U.S. Cl.
CPC ............ *A61B 18/1815* (2013.01); *A61B 5/0507* (2013.01); *A61B 5/4836* (2013.01); *A61B 18/1477* (2013.01); *A61N 5/045* (2013.01); *G01R 29/0814* (2013.01); *G01R 29/0871* (2013.01); *G01R 29/0878* (2013.01); *H01Q 1/248* (2013.01); *A61B 2018/0072* (2013.01); *A61B 2018/00577* (2013.01);
(Continued)

(58) Field of Classification Search
CPC ............... A61B 2018/00636; A61B 2018/702; A61B 2018/714; A61B 2018/732; A61B 2018/761; A61B 2018/785; A61B 2018/989; A61B 2018/916; A61B 18/18; A61B 18/1815
See application file for complete search history.

(56) References Cited

U.S. PATENT DOCUMENTS 3,721,900 A    3/1973   Andrews
D263,020 S    2/1982   Rau, III
(Continued)

FOREIGN PATENT DOCUMENTS

CN    1103807 A    6/1995
DE    390937 C    3/1924
(Continued)

OTHER PUBLICATIONS

European Search Report for European Application No. 11010046.8 dated Apr. 5, 2012.
(Continued)

*Primary Examiner* — Ronald Hupczey, Jr.

(57) ABSTRACT

A method of adjusting an ablation field radiating into tissue includes the initial steps of providing an energy applicator and providing one or more microwave field-detecting needle assemblies. Each microwave field-detecting needle assembly includes one or more rectifier elements capable of detecting microwave field intensity via rectification. The method includes the steps of positioning the energy applicator and the one or more microwave field-detecting needle assemblies in tissue, transmitting energy from an energy source through the energy applicator to generate an ablation field radiating about at least a portion of the energy applicator into tissue, and adjusting the ablation field radiating about at least the portion of the energy applicator into tissue based on at least one electrical signal transmitted by the one or more microwave field-detecting needle assemblies.

6 Claims, 12 Drawing Sheets

(51) Int. Cl.
*A61N 5/04* (2006.01)
*G01R 29/08* (2006.01)
*H01Q 1/24* (2006.01)
*A61B 5/05* (2006.01)
*A61B 5/00* (2006.01)
*A61B 18/00* (2006.01)

(52) U.S. Cl.
CPC ............... *A61B 2018/00642* (2013.01); *A61B 2018/00702* (2013.01); *A61B 2018/00714* (2013.01); *A61B 2018/00755* (2013.01); *A61B 2018/00761* (2013.01); *A61B 2018/00767* (2013.01); *A61B 2018/1425* (2013.01); *A61B 2018/1823* (2013.01); *A61B 2018/1869* (2013.01); *Y10T 29/49117* (2015.01)

(56) References Cited

U.S. PATENT DOCUMENTS

| | | | |
|---|---|---|---|
| 4,494,539 | A | 1/1985 | Zenitani et al. |
| D295,893 | S | 5/1988 | Sharkany et al. |
| D295,894 | S | 5/1988 | Sharkany et al. |
| 4,960,109 | A | 10/1990 | Lele |
| D424,694 | S | 5/2000 | Tetzlaff et al. |
| D425,201 | S | 5/2000 | Tetzlaff et al. |
| D449,886 | S | 10/2001 | Tetzlaff et al. |
| D457,958 | S | 5/2002 | Dycus et al. |
| D457,959 | S | 5/2002 | Tetzlaff et al. |
| 6,478,793 | B1 | 11/2002 | Cosman et al. |
| D496,997 | S | 10/2004 | Dycus et al. |
| D499,181 | S | 11/2004 | Dycus et al. |
| 7,025,765 | B2 | 4/2006 | Balbierz et al. |
| D525,361 | S | 7/2006 | Hushka |
| D531,311 | S | 10/2006 | Guerra et al. |
| D533,942 | S | 12/2006 | Kerr et al. |
| D535,027 | S | 1/2007 | James et al. |
| D541,418 | S | 4/2007 | Schechter et al. |
| D541,938 | S | 5/2007 | Kerr et al |
| D564,662 | S | 3/2008 | Moses et al. |
| D606,203 | S | 12/2009 | Husheer et al. |
| D613,412 | S | 4/2010 | DeCarlo |
| 8,430,871 | B2 * | 4/2013 | Brannan ............. A61B 18/18 606/33 |
| 9,055,957 | B2 | 6/2015 | Brannan |
| 2006/0289528 | A1 | 12/2006 | Chiu et al. |
| 2009/0076492 | A1 | 3/2009 | Behnke |
| 2010/0145328 | A1 * | 6/2010 | Hancock ............. A61B 18/1815 606/33 |
| 2010/0268218 | A1 * | 10/2010 | Ormsby ............. A61B 18/18 606/33 |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 836 868 A2 | 4/1998 |
| EP | 0 882 955 A1 | 12/1998 |
| EP | 1159926 A3 | 3/2003 |
| EP | 2264828 A1 | 12/2010 |
| EP | 2298211 A1 | 3/2011 |
| EP | 2316370 A1 | 5/2011 |
| EP | 2407205 A1 | 1/2012 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| GB | 2434872 A | 8/2007 |
| GB | 2467604 A | 8/2010 |
| JP | S6329666 A | 2/1988 |
| JP | 5-5106 | 1/1993 |
| JP | 05-40112 | 2/1993 |
| JP | 06343644 A | 12/1994 |
| JP | H07185019 A | 7/1995 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 2008071914 A2 | 6/2008 |
| WO | 2010/035831 A1 | 4/2010 |
| WO | 2010092328 A1 | 8/2010 |

OTHER PUBLICATIONS

European Search Report for European Application No. 11010024.5 dated Apr. 16, 2012.
U.S. Appl. No. 12/582,857, filed Oct. 21, 2009, Charles D. Allen.
U.S. Appl. No. 12/606,769, filed Oct. 27, 2009, Joseph D. Brannan.
U.S. Appl. No. 12/607,221, filed Oct. 28, 2009, Joseph D. Brannan.
U.S. Appl. No. 12/607,268, filed Oct. 28, 2009, Joseph D. Brannan.
U.S. Appl. No. 12/619,323, filed Nov. 16, 2009, Arnold V. DeCarlo.

(56) References Cited

OTHER PUBLICATIONS

U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/877,182, filed Sep. 8, 2010, Robert B. Cunningham.
U.S. Appl. No. 12/910,442, filed Oct. 22, 2010, Robert B. Cunningham.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.

(56) References Cited

OTHER PUBLICATIONS

Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With no Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vase. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Humphries Jr. et al., "Finite.cndot.Element Codes to Model Electrical Heating and Non.cndot.L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.

(56) References Cited

OTHER PUBLICATIONS

International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report, Application No. EP 14 17 1496, dated Aug. 12, 2014.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences. cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.-Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.

(56) References Cited

OTHER PUBLICATIONS

European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
Notice of Reasons for Rejection from Japanese Appl. No. 2011-276800 mailed Oct. 6, 2015.

\* cited by examiner

METHODS OF ADJUSTING AN ABLATION FIELD RADIATING INTO TISSUE USING MICROWAVE FIELD-DETECTING NEEDLE ASSEMBLIES

CROSS-REFERENCE TO RELATED APPLICATIONS

This application is a divisional application of U.S. application Ser. No. 12/977,390, filed on Dec. 23, 2010, now U.S. Pat. No. 9,055,957, the entire contents of which being incorporated by reference herein

BACKGROUND

1. Technical Field

The present disclosure relates to electrosurgical devices suitable for use in tissue ablation applications and, more particularly, to microwave field-detecting needle assemblies, methods of manufacturing the same, methods of adjusting an ablation field radiating into tissue using the same, and systems including the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source and a microwave surgical instrument (e.g., microwave ablation probe) having an antenna assembly for directing energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

The particular type of tissue ablation procedure may dictate a particular ablation volume in order to achieve a desired surgical outcome. Ablation volume is correlated with antenna design, antenna performance, antenna impedance, ablation time and wattage, and tissue characteristics, e.g., tissue impedance.

Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to surrounding normal tissue. In some cases, it may be difficult for the physician to determine when a microwave ablation probe is inserted to a proper depth within tissue, e.g., to reach the location of the ablation site and/or to avoid unintended radiation exposure.

SUMMARY

The present disclosure relates to method of adjusting an ablation field radiating into tissue including the initial steps of providing an energy applicator and providing one or more microwave field-detecting needle assemblies. Each microwave field-detecting needle assembly includes one or more rectifier elements capable of detecting microwave field intensity via rectification. The method includes the steps of positioning the energy applicator and the one or more microwave field-detecting needle assemblies in tissue, transmitting energy from an energy source through the energy applicator to generate an ablation field radiating about at least a portion of the energy applicator into tissue, and adjusting the ablation field radiating about at least the portion of the energy applicator into tissue based on at least one electrical signal transmitted by the one or more microwave field-detecting needle assemblies.

The present disclosure also relates to method of adjusting an ablation field radiating into tissue including the initial steps of providing an energy applicator operably coupled to an energy source and providing one or more microwave field-detecting needle assemblies. Each microwave field-detecting needle assembly includes one or more rectifier elements capable of detecting microwave field intensity via rectification. The method includes the steps of positioning the energy applicator and the one or more microwave field-detecting needle assemblies in tissue, transmitting energy from the energy source through the energy applicator to generate an ablation field radiating about at least a portion of the energy applicator into tissue, and adjusting the ablation field radiating about at least the portion of the energy applicator into tissue by adjusting at least one operating parameter associated with the energy source based on at least one electrical signal transmitted by the one or more microwave field-detecting needle assemblies.

The present disclosure also relates to a microwave ablation control system including a microwave field-detecting needle assembly and a control unit in operable communication with the microwave field-detecting needle assembly. The microwave field-detecting needle assembly includes at least one rectifier element capable of detecting microwave field intensity via rectification. The microwave ablation control system also includes an electrosurgical power generating source in operable communication with the control unit and an energy-delivery device operably coupled to the electrosurgical power generating source.

BRIEF DESCRIPTION OF THE DRAWINGS

Objects and features of the presently-disclosed microwave field-detecting needle assemblies, methods of manufacturing the same, methods of adjusting an ablation field radiating into tissue using the same, and systems including the same will become apparent to those of ordinary skill in the art when descriptions of various embodiments thereof are read with reference to the accompanying drawings, of which:

FIG. 17 is a perspective view of a second side of the needle assembly of.

FIG. 16 according to an embodiment of the present disclosure;

DETAILED DESCRIPTION

Figure 1:
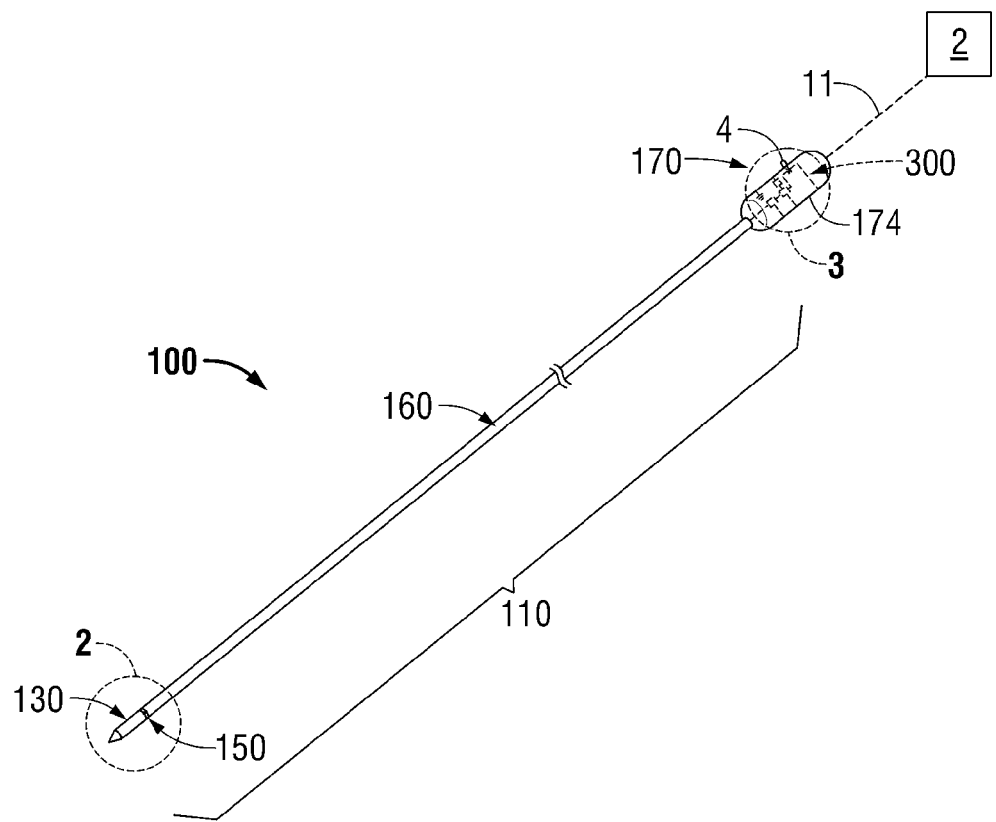
FIG. 1 is a perspective view of microwave field-detecting needle assembly including a needle assembly and a handle assembly according to an embodiment of the present disclosure.

Hereinafter, embodiments of microwave field-detecting needle assemblies, methods of manufacturing the same, methods of adjusting an ablation field radiating into tissue using the same, and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "transmission line" generally refers to any transmission medium that can be used for the propagation of signals from one point to another.

As it is used in this description, "ablation procedure" generally refers to any ablation procedure, such as, for example, microwave ablation, radiofrequency (RF) ablation, or microwave or RF ablation-assisted resection. As it is used in this description, "energy applicator" generally refers to any device that can be used to transfer energy from a power generating source, such as a microwave or RF electrosurgical generator, to tissue. For the purposes herein, the term "energy applicator" is interchangeable with the term "energy-delivery device".

As it is used in this description, "rectifier" generally refers to circuit components that allow more electric current to flow in one direction than in the other. Rectifiers may be made of solid-state diodes, vacuum-tube diodes, mercury-arc valves, and other components. Processes that make use of rectifiers include rectification, which, simply defined, is the conversion of alternating current (AC) to direct current (DC). As it is used in this description, "diode" generally refers to electronic devices that allow electric current to flow in only one direction, while inhibiting current flow in the other. For the purposes herein, the term "diode" is interchangeable with the term "rectifier".

As it is used in this description, "printed circuit board" (or "PCB") generally refers to any and all systems that provide, among other things, mechanical support to electrical components, electrical connection to and between these electrical components, combinations thereof, and the like.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide microwave field-detecting needle assemblies adapted to enable physicians to detect microwave field intensity in proximity to an energy-delivery devices, e.g., to ensure patient and/or physician safety and/or to provide for improved control over applied energy. Microwave field-detecting needle assembly embodiments may be implemented as passive devices. In some embodiments, microwave field-detecting needle assemblies may be monitored by a stand-alone control unit. Microwave field-detecting needle assembly embodiments may be integrated into a feedback control loop within a microwave ablation control system.

Microwave field-detecting needle assembly embodiments may be suitable for utilization in open surgical applications. Embodiments may be used in minimally invasive procedures, e.g., endoscopic and laparoscopic surgical procedures. Portions of the presently-disclosed microwave field-detecting needle assemblies may be disposable, replaceable and/or reusable.

Figure 4:
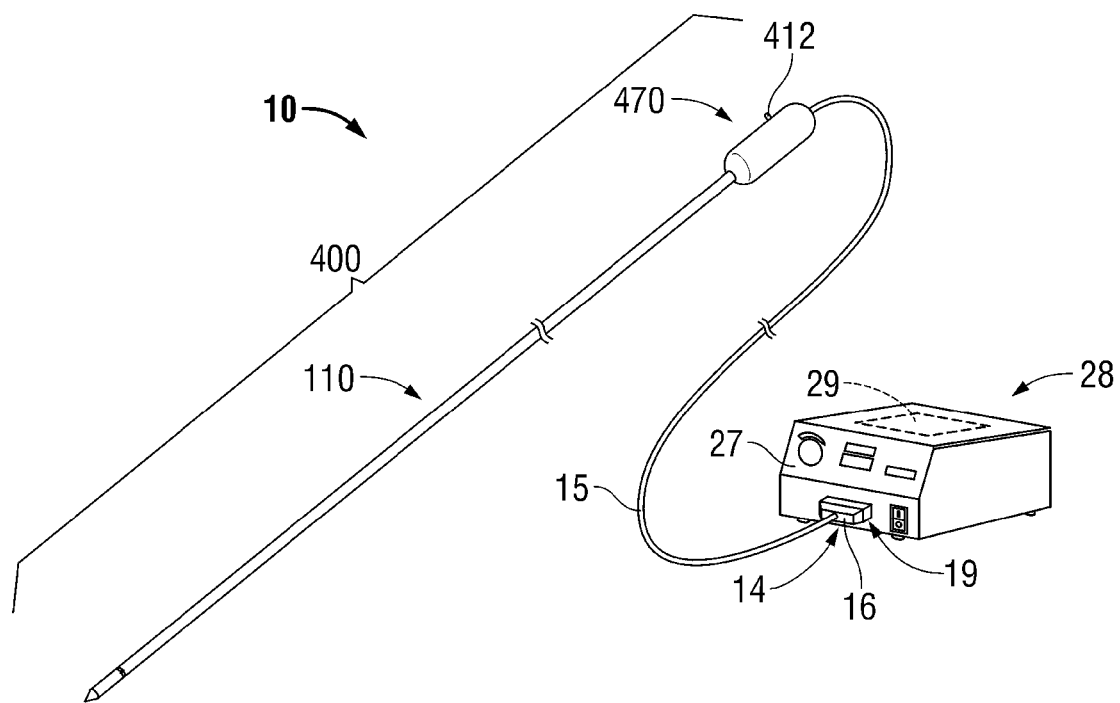
FIG. 4 is perspective view of a microwave field-detecting system including an embodiment of a microwave field-detecting needle assembly and an embodiment of a control unit in accordance with the present disclosure.

Various embodiments of the presently-disclosed microwave field-detecting needle assembly are adapted to be coupled in communication with a stand-alone control unit (e.g., 28 shown in FIG. 4).

An electrosurgical system (also referred to herein as a "microwave ablation control system") including an energy-delivery device(s) and one or more microwave field-detecting needle assemblies according to various embodiments is designed and configured to operate at frequencies between about 300 MHz and about 10 GHz. The presently-disclosed microwave ablation control systems are suitable for microwave or RF ablation and for use to pre-coagulate tissue for microwave or RF ablation-assisted surgical resection. In addition, although the following description describes embodiments of a microwave field-detecting needle assembly capable of detecting electromagnetic radiation at microwave frequencies, the teachings of the present disclosure may also apply to electromagnetic radiation at RF frequencies or at other frequencies.

Figure 2:
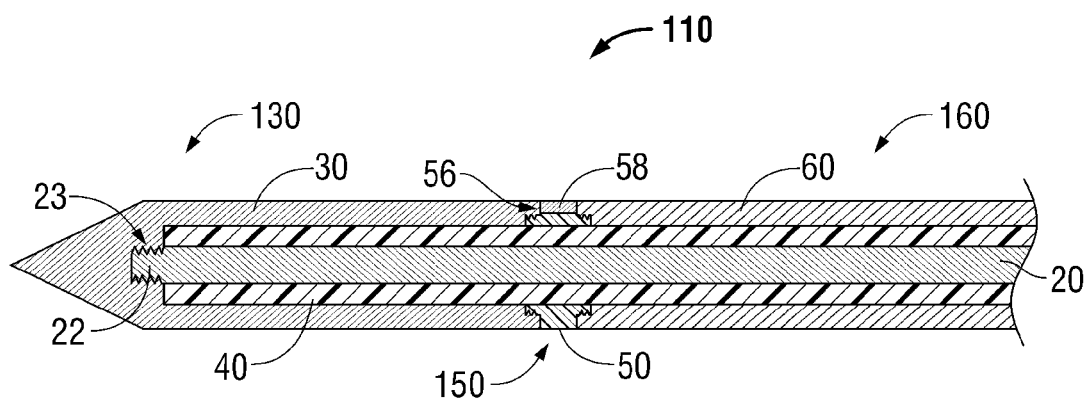
FIG. 2 is an enlarged, cross-sectional view of the indicated area of detail of FIG. 1 showing a distal portion of the needle assembly according to an embodiment of the present disclosure.
Figure 3:
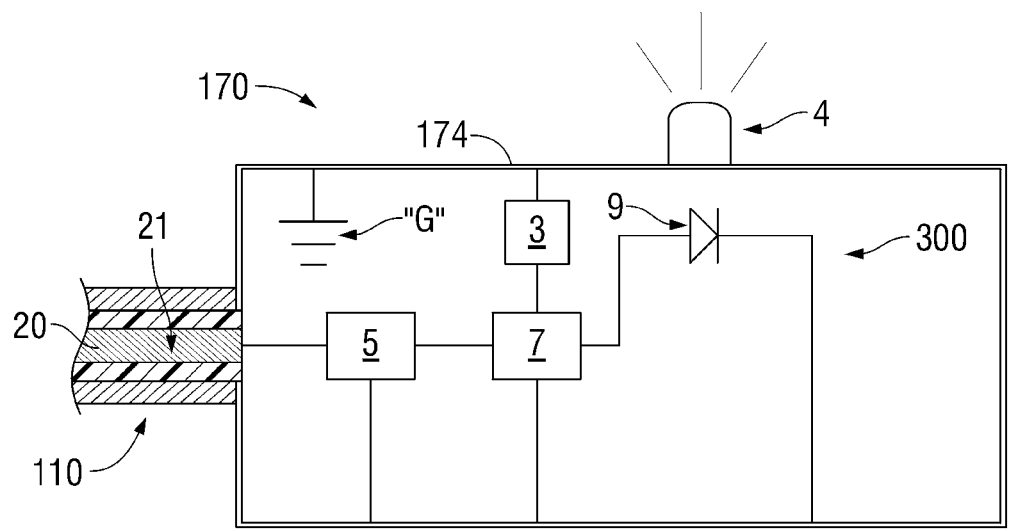
FIG. 3 is an enlarged view of the indicated area of detail of FIG. 1 showing a schematic diagram of an electric circuit (shown in phantom lines in FIG. 1) disposed within the handle assembly according to an embodiment of the present disclosure.

FIGS. 1 through 3 show an embodiment of a microwave field-detecting needle assembly (shown generally as 100 in FIG. 1). Microwave field-detecting needle assembly 100 generally includes a handle assembly 170 and a needle assembly 110. FIG. 3 shows a schematic diagram of an electric circuit 300 (shown in phantom lines in FIG. 1) disposed within a handle housing 174 of the handle assembly 170. Needle assembly 110 is shown with parts separated in FIG. 5.

Figure 5:
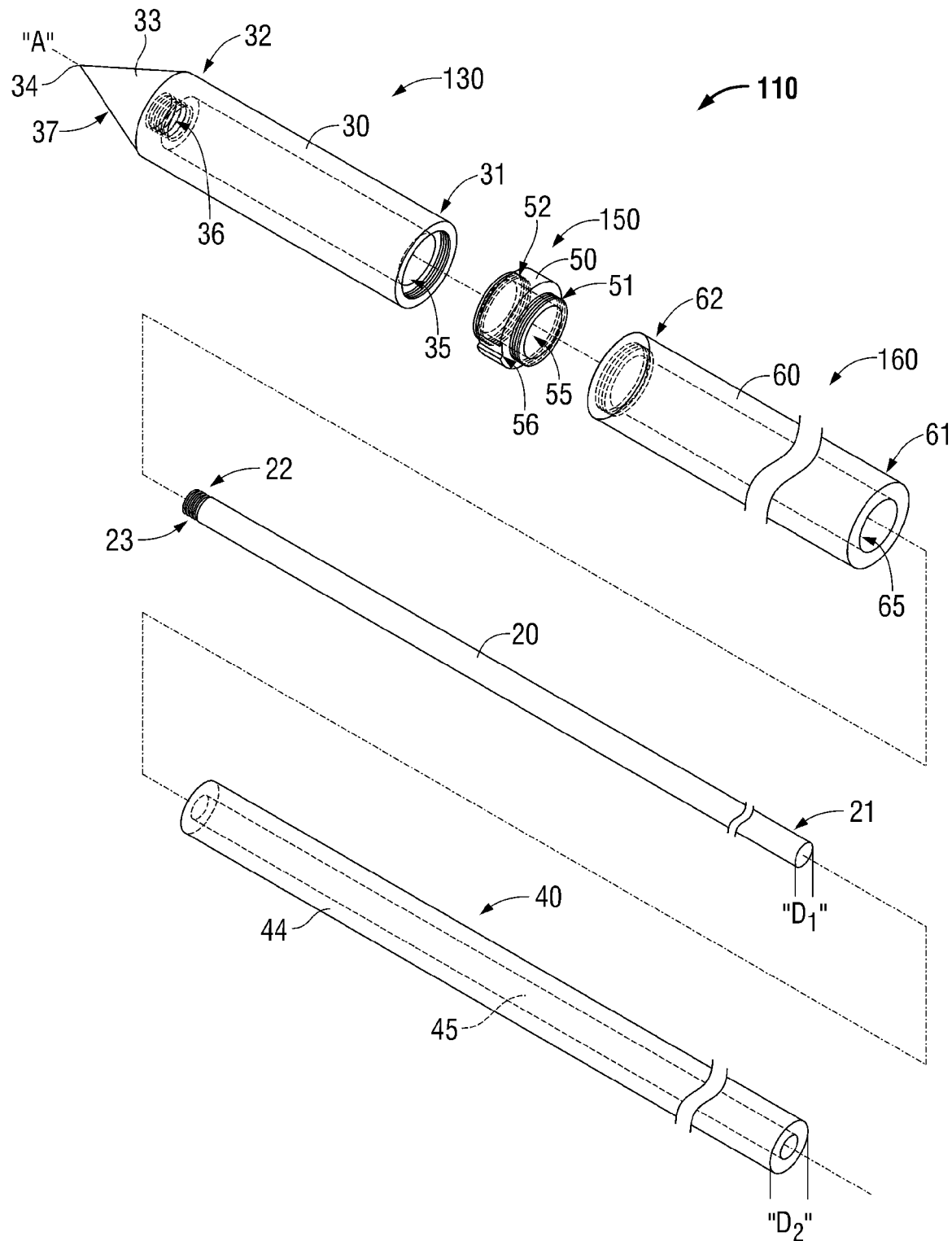
FIG. 5 is perspective view with parts separated of the microwave field-detecting needle assembly of FIG. 1 according to an embodiment of the present disclosure.

As shown in FIGS. 1, 2 and 5, the needle assembly 110 generally includes a distal portion 130, a proximal portion 160, and a junction member 150 disposed between the distal portion 130 and the proximal portion 160. In some embodiments, the distal portion 130 and the proximal portion 160 align at the junction member 150, which is generally made of a dielectric material. In some embodiments, the junction member 150 may be configured to be mechanically coupleable (e.g., threadedly coupleable) to the distal portion 130 and/or the proximal portion 160. In some embodiments, the distal portion 130 includes a first outer-conductor structure 30, the proximal portion 160 includes a second outer-conductor structure 60, and the junction member 150 includes a junction structure 50. The shape and size of the needle assembly 110 and the handle assembly 170 may be varied from the configuration depicted in FIG. 1.

As shown in FIGS. 2 and 5, needle assembly 110 includes an inner-conductor pin 20, a tubular sleeve member 40 disposed around at least a portion of the inner-conductor pin 20, a first outer-conductor structure 30, a second outer-conductor structure 60, a junction structure 50 disposed between the first outer-conductor structure 30 and the second outer-conductor structure 60, and one or more rectifiers 58 disposed in one or more recesses 56 defined in the junction structure 50. Inner-conductor pin 20 has a suitable outer diameter "$D_1$" (FIG. 5). The distal end 22 of the inner-conductor pin 20 includes a retaining portion 23. In some embodiments, the retaining portion 23 may be externally threaded. In one embodiment, the proximal end 21 of the inner-conductor pin 20 is coupled to the handle assembly 170. Inner-conductor pin 20 may be electrically coupled to an electric circuit 300, which is described in more detail later in this disclosure, disposed within the handle assembly 170.

Various components of the needle assembly 110 may be formed of suitable, electrically-conductive materials, e.g., copper, gold, silver, or other conductive metals or metal alloys having similar conductivity values. Electrically-conductive materials used to form the inner-conductor pin 20, the first outer-conductor structure 30 and/or the second outer-conductor structure 60 may be plated with other materials, e.g., other conductive materials, such as gold or silver, to improve their properties, e.g., to improve conductivity, decrease energy loss, etc.

In some embodiments, the inner-conductor pin 20, the first outer-conductor structure 30 and/or the second outer-conductor structure 60 may be formed of a rigid, electrically-conductive material, such as stainless steel. In some embodiments, the inner-conductor pin 20 is formed from a first electrically-conductive material (e.g., stainless steel) and the first outer-conductor structure 30 and/or the second outer-conductor structure 60 is formed from a second electrically-conductive material (e.g., copper). In some embodiments, the inner-conductor pin 20, the first outer-conductor structure 30 and/or the second outer-conductor structure 60 may be formed of a flexible, electrically-conductive material, such as titanium.

Tubular sleeve member 40 includes a body 44 that defines a longitudinally-extending internal bore or chamber 45 configured to receive at least a portion of the inner-conductor pin 20 therein. Body 44 has a suitable outer diameter "$D_2$" as shown in FIG. 5. Tubular sleeve member 40 may be formed from any suitable dielectric material, including, but not limited to, ceramics, mica, polyethylene, polyethylene terephthalate, polyimide, polytetrafluoroethylene (PTFE) (e.g., TEFLON®, manufactured by E. I. du Pont de Nemours and Company of Wilmington, Del., United States), glass, metal oxides or other suitable insulator, and may be formed in any suitable manner. In the embodiment shown in FIG. 2, tubular sleeve member 40 is disposed around a length of the inner-conductor pin 20 proximal to the retaining portion 23.

Junction member embodiments in accordance with the present disclosure include a junction structure having one or more recesses (e.g., one recess 56 shown in FIGS. 2, 5 and 9-12, or a plurality of recesses 1656 shown in FIG. 16) defined therein. As best shown in FIG. 11, the recess 56 is configured to receive a rectifier 58 therein. Rectifier 58 may include one or more diodes, e.g., Zener diode, Schottky diode, tunnel diode and the like, and/or other suitable component(s) capable of converting AC to DC.

Junction structure 50 may be formed of any suitable elastomeric or ceramic dielectric material by any suitable process. In some embodiments, the junction structure 50 may be formed of a composite material having low electrical conductivity, e.g., glass-reinforced polymers. In some embodiments, the junction structure 50 is formed by over-molding and includes a thermoplastic elastomer, such as, for example, polyether block amide (e.g., PEBAX®, manufactured by The Arkema Group of Colombes, France), polyetherimide (e.g., ULTEM® and/or EXTEM®, manufactured by SABIC Innovative Plastics of Saudi Arabia) and/or polyimide-based polymer (e.g., VESPEL®, manufactured by E. I. du Pont de Nemours and Company of Wilmington, Del., United States). Junction structure 50 may be formed using any suitable over-molding compound by any suitable process, and may include use of a ceramic substrate.

In an embodiment, as best shown in FIG. 3, electric circuit 300 is disposed within the handle housing 174 of the handle assembly 170. In one embodiment, electric circuit 300 may be formed as a printed circuit board, with components thereof connected by traces on an epoxy resin substrate.

Handle housing 174 provides a ground reference "G" for the circuit 300. An indicator unit 4, or component thereof, is coupled to the handle housing 174. Indicator unit 4 may include audio and/or visual indicator devices to provide information/feedback to a user. In the embodiment shown in FIGS. 1 and 3, the indicator unit 4 is adapted to generate a visual signal and includes a light source, such as a light-emitting diode 9. Indicator unit 4 may additionally, or alternatively, be adapted to generate an audio signal and may include an audio circuit with a speaker (not shown).

The proximal end 21 of the inner-conductor pin 20 (shown in cross section in FIG. 3) is electrically coupled to a first terminal of a filter circuit 5. Filter circuit 5 includes a second terminal electrically coupled to an amplifier circuit 7, and may include a ground terminal electrically coupled to the handle housing 174. Filter circuit 5 may include an RF filter block. In one embodiment, the filter circuit 5 may be an inductor-resistor-capacitor (LCR) low-pass filter that is adapted to convert a rectified sinusoidal waveform from the rectifier element(s) 58 into an electrical signal, which may be a DC voltage signal representative of the detected microwave field intensity.

As shown in FIG. 3, circuit 300 includes a power source 3 that is electrically coupled to the amplifier circuit 7. Power source 3 may include a ground terminal electrically coupled to the handle housing 174. Power source 3 may include any combination of battery cells, a battery pack, fuel cell and/or high-energy capacitor. A battery pack may include one or more disposable batteries. In such case, the one or more disposable batteries may be used as a primary power source for the amplifier circuit 7. In some embodiments, a transmission line 11 (FIG. 1) is provided to connect the microwave field-detecting needle assembly to a line source voltage or external power source (shown generally as 2 in FIG. 1), in which case a battery pack may be provided for use as a backup power source.

FIG. 4 schematically illustrates an embodiment of a microwave field-detecting system (shown generally as 10) that includes a stand-alone control unit 28 operably coupled to a microwave field-detecting needle assembly 400. Microwave field-detecting needle assembly 400 is similar to the microwave field-detecting needle assembly 100 of FIG. 1, except that microwave field-detecting needle assembly 400 includes a handle assembly 470 configured to operably couple the needle assembly 110 to a cable assembly 15. Cable assembly 15 may be any suitable transmission line. Cable assembly 15 may include a proximal end 14 suitable for connection to the control unit 28.

Handle assembly 470 includes an indicator unit 412 that is suitably configured to provide information/feedback to a user. Indicator unit 412 is similar to the indicator unit 4 shown in FIG. 3 and further description thereof is omitted in the interests of brevity. The shape and size of the handle assembly 470 and the indicator unit 412 may be varied from the configuration depicted in FIG. 4.

Control unit 28 may include a user interface 27 in operable communication with a processor unit 29. User interface 27 may include audio and/or visual indicator devices to provide information/feedback to a user. Processor unit 29 may be any type of computing device, computational circuit, or any type of processor or processing circuit capable of executing a series of instructions that are stored in a memory (not shown) associated with the processor unit 29. Processor unit 29 may be adapted to run an operating system platform and application programs. Microwave field-detecting needle assembly 400 and the control unit 28 may utilize wired communication and/or wireless communication. In the embodiment illustrated in FIG. 4, the microwave field-detecting needle assembly 400 is electrically connected via the cable assembly 15 to a connector 16, which further operably connects the microwave field-detecting needle assembly 400 to a terminal 19 of the control unit 28.

FIG. 5 shows the needle assembly 110 with parts separated in accordance with the present disclosure. As described above with reference to FIG. 2, the needle assembly 110 includes an inner-conductor pin 20, first outer-conductor structure 30, second outer-conductor structure 60, tubular sleeve member 40, junction structure 50, and one or more rectifiers 58.

As shown in FIG. 5, the first outer-conductor structure 30 defines a first chamber portion 36 and a second chamber portion 35. First chamber portion 36 is disposed at the distal end 32 of the first outer-conductor structure 30. Second chamber portion 35 is disposed in communication with the first chamber portion 36 and includes an opening disposed at the proximal end 31 of the first outer-conductor structure 30. In some embodiments, the first chamber portion 36 is configured to matingly engage, e.g., threadedly engage, with the retaining portion 23 of inner-conductor pin 20, and the second chamber portion 35 is configured to receive at least a portion of the tubular sleeve member 40 therein.

First outer-conductor structure 30 may be provided with an end cap 37. End cap 37 generally includes a tapered portion 33, which may terminate in a sharp tip 34 to allow for insertion into tissue with minimal resistance. Tapered portion 33 may include other shapes, such as, for example, a tip 34 that is rounded, flat, square, hexagonal, or cylindroconical. End cap 37 may be formed of a material having a high dielectric constant, and may be a trocar, e.g., a zirconia ceramic. First outer-conductor structure 30 and end cap 37 may be formed separately from each other, and coupled together, e.g., with the aid of adhesive or solder. First outer-conductor structure 30 and end cap 37 may form a single, unitary structure. The shape and size of the first outer-conductor structure 30 and the end cap 37 may be varied from the configuration depicted in FIG. 5.

Second outer-conductor structure 60 defines a longitudinally-extending internal bore or chamber 65 that extends from the proximal end 61 to the distal end 62 of the second outer-conductor structure 60. Chamber 65 is configured to receive at least a portion of the tubular sleeve member 40 therein.

Junction structure 50 defines a longitudinally-extending internal bore or chamber 55 therein and generally includes a distal end 52 adapted for connection to the first outer-conductor structure 30 and a proximal end 51 adapted for connection to the second outer-conductor structure 60. In some embodiments, the junction structure 50 includes a distal end 52 provided with a series of external threads configured to matingly engage with a series of internal threads disposed at the proximal end 31 of the first outer-conductor structure 30, and a proximal end 51 provided with a series of external threads configured to matingly engage with a series of internal threads disposed at the distal end 62 of the second outer-conductor structure 60. The shape and size of the junction structure 50 may be varied from the configuration depicted in FIG. 5.

Figure 6:
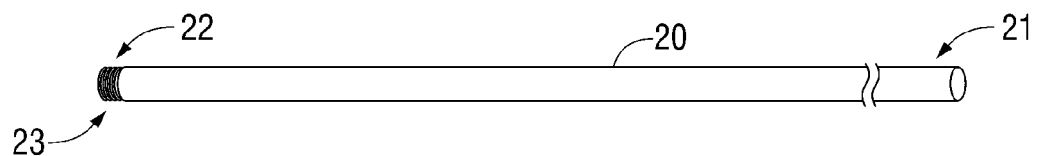
FIG. 6 is perspective view of an inner-conductor pin including a distal end configured with a retaining portion according to an embodiment of the present disclosure.

FIGS. 6 through 13 show a sequentially-illustrated, assembly of components forming the needle assembly 110 in accordance with the present disclosure. FIG. 6 shows the inner-conductor pin 20. As described above, inner-conductor pin 20 may be formed of any suitable electrically-conductive material (e.g., metal such as stainless steel, aluminum, titanium, copper, etc.) of any suitable length. The shape and size of the inner-conductor pin 20 may be varied from the configuration depicted in FIG. 6.

Figure 7:
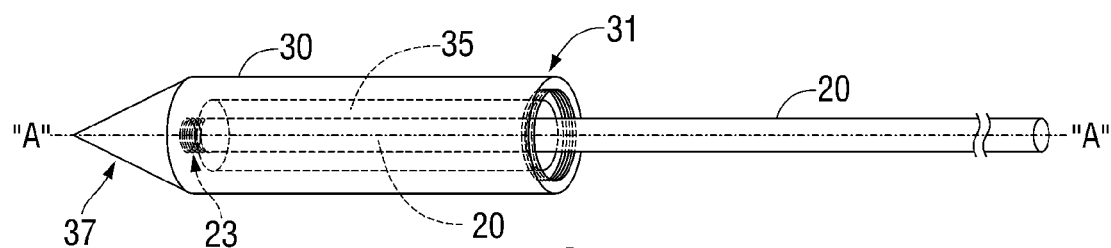
FIG. 7 is perspective view of a portion of a needle assembly including a first outer-conductor structure coupled to the retaining portion and disposed around a distal portion of the inner-conductor pin shown in FIG. 6 according to an embodiment of the present disclosure.

As cooperatively shown in FIGS. 6 and 7, inner-conductor pin 20 includes a distal end 22 including a retaining portion 23 that is configured to be connectable, e.g., electrically and mechanically, to the first outer-conductor structure 30. In some embodiments, the retaining portion 23 is provided with a series of external threads configured to matingly engage with a series of internal threads disposed within the first chamber portion 36 of the first outer-conductor structure 30. Alternatively, mechanical fasteners, grooves, flanges, adhesives, and welding processes, e.g., laser welding, or other suitable joining method may be used to attach (or clip, connect, couple, fasten, secure, etc.) the inner-conductor pin 20 to the first outer-conductor structure 30. As shown in FIG. 7, a longitudinal axis "A"-A" is defined by the inner-conductor pin 20.

Figure 8:
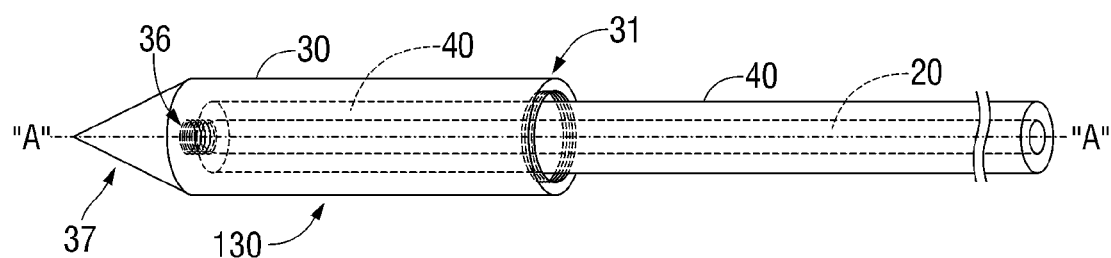
FIG. 8 is a perspective view of the portion of the needle assembly of FIG. 7 shown with a tubular sleeve member disposed around a length of the inner-conductor pin proximal to the threaded portion according to an embodiment of the present disclosure.
Figure 9:
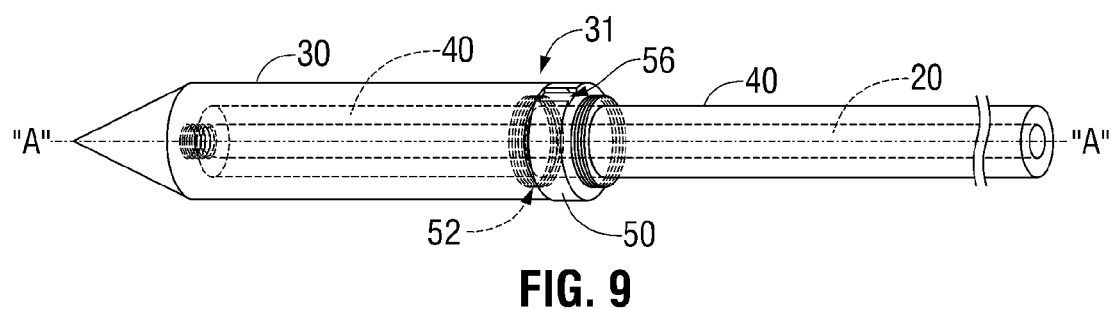
FIG. 9 is a perspective view of the portion of the needle assembly of FIG. 8 shown with a junction structure disposed around a portion of the tubular sleeve member and threadedly coupled to the proximal end of the first outer-conductor structure according to an embodiment of the present disclosure.
Figure 10:
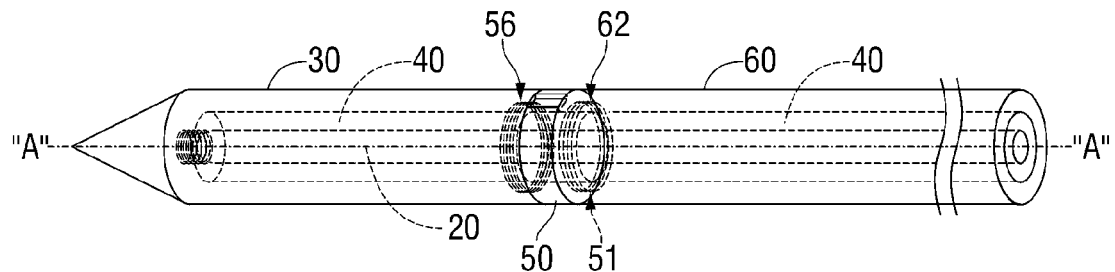
FIG. 10 is a perspective view of the portion of the needle assembly of FIG. 9 shown with a second outer-conductor structure disposed around a proximal portion of the tubular sleeve member and threadedly coupled to the distal end of the junction structure, according to an embodiment of the present disclosure.
Figure 11:
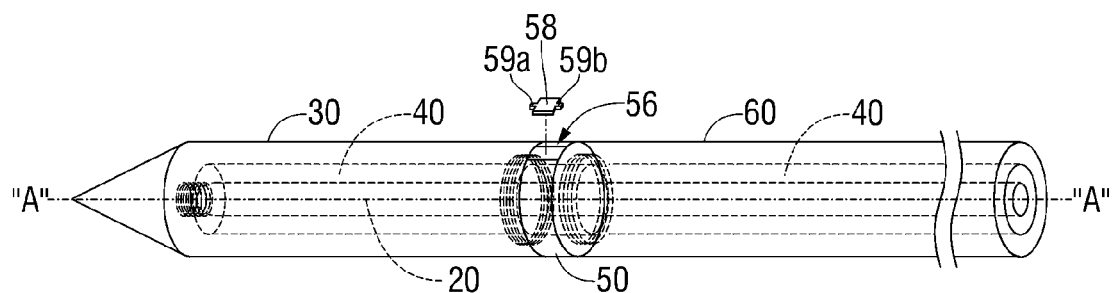
FIG. 11 is a perspective view of the portion of the needle assembly of FIG. 10 shown with a rectifier element disposed separately from and positioned above a rectifier-receiving recess defined in the junction structure according to an embodiment of the present disclosure.

As cooperatively shown in FIGS. 8 through 10, tubular sleeve member 40 is configured to be receivable within second chamber portion 35 of the first outer-conductor structure 30, chamber 55 of the junction structure 50 and chamber 60 of the second outer-conductor structure 60. FIG. 8 shows the tubular sleeve member 40 joined together with the inner-conductor pin 20 and the first outer-conductor structure 30 such that the tubular sleeve member 40 is coaxially-disposed about the length of the inner conductor 20 proximal to the retaining portion 23 and disposed at least in part within the second chamber portion 35 of the first outer-conductor structure 30. In an embodiment, the tubular sleeve member 40 is positioned around the inner-conductor pin 20 after the retaining portion 23 is coupled to the end cap 37, e.g., as shown in FIG. 8. Tubular sleeve member 40 may, alternatively, be positioned, formed, adhered or otherwise disposed around at least a portion of the inner-conductor pin 20 prior to the introduction of the inner-conductor pin 20 into the second chamber portion 35 of the first outer-conductor structure 30.

FIG. 9 shows the portion of the needle assembly of FIG. 8 shown with junction structure 50 disposed around a portion of the tubular sleeve member 40 and coupled to the first outer-conductor structure 30. Junction structure 50 may be coupled to the first outer-conductor structure 30 by any suitable manner of connection. In the embodiment shown in FIG. 9, junction structure 50 includes a distal end 52 provided with a series of external threads configured to matingly engage with a series of internal threads disposed at the proximal end 31 of the first outer-conductor structure 30. The junction structure 50 and the first outer-conductor structure 30 (as well as other components described herein) may be assembled together with the aid of alignment pins, snap-like interfaces, tongue and groove interfaces, locking tabs, adhesive ports, etc., utilized either alone or in combination for assembly purposes.

FIG. 10 shows the portion of the needle assembly of FIG. 9 shown with second outer-conductor structure 60 disposed around a portion of the tubular sleeve member 40 and coupled to the proximal end 51 of the junction structure 50. In the embodiment shown in FIG. 10, second outer-conductor structure 60 includes a distal end 62 provided with a series of internal threads configured to matingly engage with a series of external threads disposed at the proximal end 51 of the junction structure 50.

FIG. 11 shows the portion of the needle assembly of FIG. 10 shown with rectifier element 58 disposed above rectifier-receiving recess 56 in the junction structure 50. Rectifier element 58 includes a first lead wire or pin 59a (also referred to herein as a "terminal") and a second lead wire or pin 59b. Rectifier-receiving recess 56 may be configured to receive the rectifier element 58 such that the first pin 59a and the second pin 59b are substantially aligned with the longitudinal axis "A"-A" defined by the inner-conductor pin 20.

Figure 12:
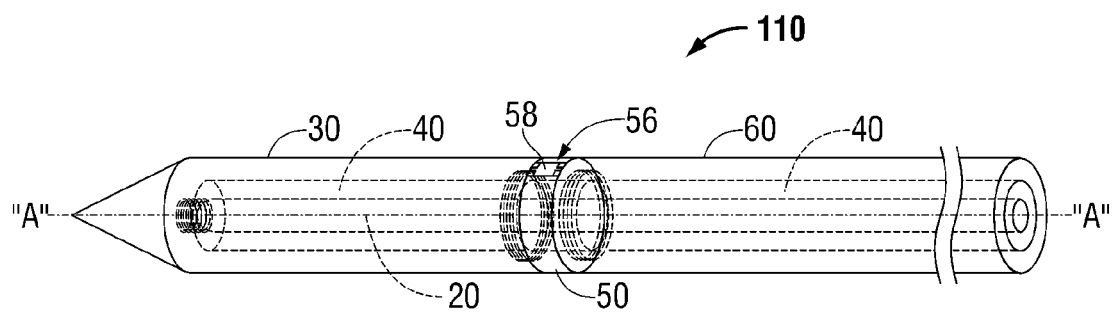
FIG. 12 is a perspective view of the portion of the needle assembly of FIG. 11 shown with the rectifier element disposed in the rectifier-receiving recess according to an embodiment of the present disclosure.

FIG. 12 shows the portion of the needle assembly of FIG. 11 shown with the rectifier element 58 disposed in the rectifier-receiving recess 56. First pin 59a is electrically coupled to the first outer-conductor structure 30 by any suitable manner of electrical connection, e.g., soldering, welding, or laser welding. Second pin 59b is electrically coupled to the second outer-conductor 60 by any suitable manner of electrical connection.

Figure 13:
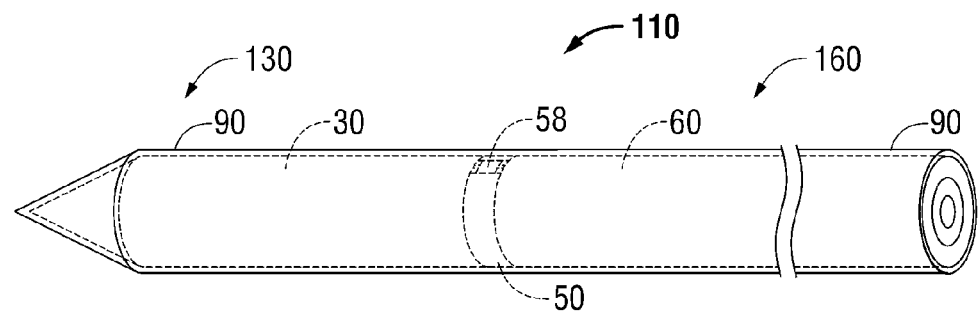
FIG. 13 is a perspective view of the portion of the needle assembly of FIG. 12 shown with an outer jacket disposed around the first outer-conductor structure, second outer-conductor structure and the junction structure according to an embodiment of the present disclosure.

FIG. 13 shows the portion of the needle assembly of FIG. 12 shown with an outer jacket 90 disposed around the first outer-conductor structure 30, the second outer-conductor structure 60, and the junction structure 50. Outer jacket 90 may be formed of any suitable material, such as, for example, polymeric or ceramic materials. The outer jacket 90 may be applied by any suitable method, such as, for example, heat-shrinkage, extrusion, molding, coating, spraying, dipping, powder coating, baking and/or film deposition, or other suitable process.

Figure 14:
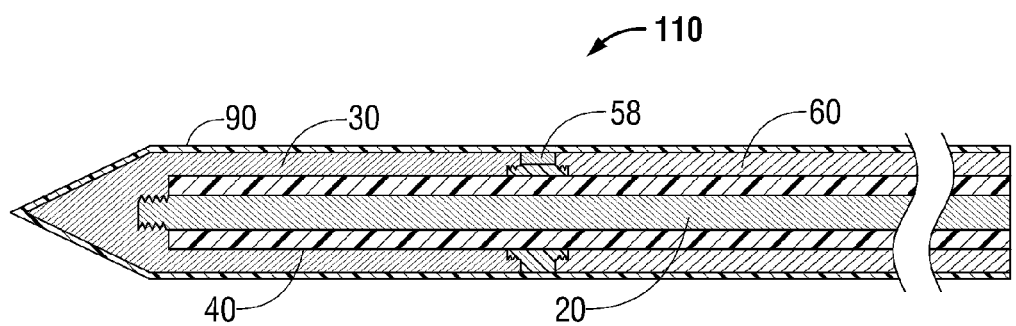
FIG. 14 is a cross-sectional view of the portion of the needle assembly of FIG. 13 according to an embodiment of the present disclosure.

In an embodiment, as best shown in FIG. 14, which shows the cross section of the needle assembly portion of FIG. 13, outer jacket 90 covers the rectifier element 58. In alternative embodiments, the outer jacket 90 may include an opening (not shown) configured to expose the rectifier element 58 and/or the junction structure 50, or portion thereof.

Figure 15:
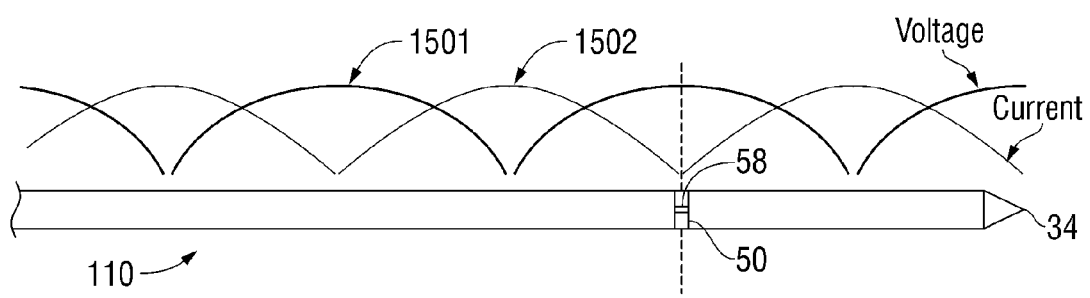
FIG. 15 is a schematically-illustrated representation of a standing wave coupled to the needle assembly of FIG. 13 according to an embodiment of the present disclosure.

The position of the junction structure 50 and rectifier element 58, e.g., in relation to the tip 34, is one factor in determining the operational frequency of the microwave field-detecting needle assembly 100 in a given material, e.g., tissue. To obtain a microwave field-detecting needle assembly having a desired frequency, the junction structure 50 may be positioned at a location of high voltage along the expected standing wave that couples onto the probe, such as illustratively shown in FIG. 15. During a procedure, e.g., an ablation procedure, fields 1501, 1502 couple onto the microwave field-detecting needle assembly 100 from the energy supplied by an energy-delivery device (e.g., 12 shown in FIG. 18), e.g., a microwave ablation probe.

Figure 16:
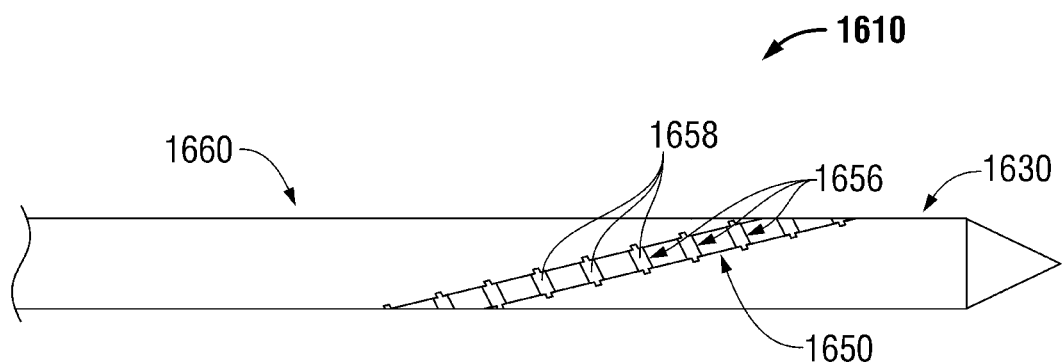
FIG. 16 is a perspective view of a first side of another embodiment of a needle assembly in accordance with the present disclosure.
Figure 17:
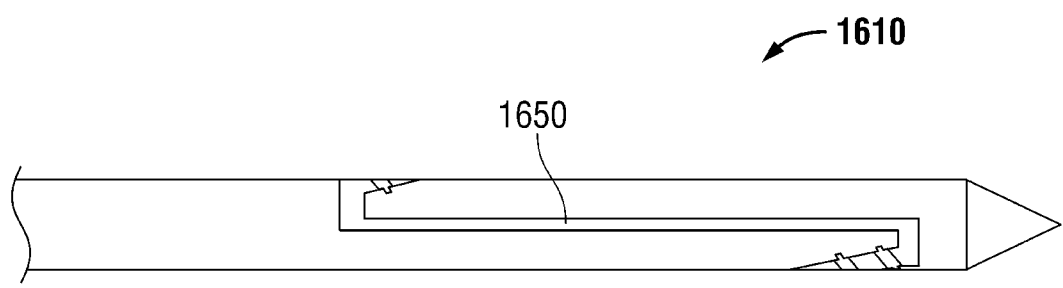

FIGS. 16 and 17 show a needle assembly (shown generally as 1610) according to an embodiment of the present disclosure that is adapted to enable multi-frequency operation and/or multiple wavelength operation. Needle assembly 1610 is similar to the needle assembly 110 shown in FIGS. 1, 2 and 5, except for the configuration of the junction structure 1650, the first outer-conductor structure 1630 and the second outer-conductor structure 1660, and the plurality of rectifiers 1658 disposed in the plurality of recesses 1656.

Needle assembly 1610 includes a junction structure 1650 configured to separate a first outer-conductor structure 1630 and a second outer-conductor structure 1660 in a diagonal fashion. First outer-conductor structure 1630 and the second outer-conductor structure 1660 may be formed of any suitable electrically-conductive material, e.g., metal such as stainless steel, aluminum, titanium, copper, or the like. In some embodiments, the first outer-conductor structure 1630 is constructed from stainless steel, and may be coated in a high electrical conductivity, corrosion-resistant metal, e.g., silver, or the like.

As best shown in FIG. 16, the junction structure 1650 includes a plurality of recesses 1656 defined therein, wherein each recess 1656 is defined in a different outer-peripheral portion of the junction structure 1650 and configured to receive a rectifier 1658 therein. Rectifier 1658 is similar to the rectifier 58 shown in FIG. 2 and further description thereof is omitted in the interests of brevity. Each rectifier 1658 may be configured to operate efficiently at separate frequencies allowing for probe use at multiple frequencies.

Figure 18:
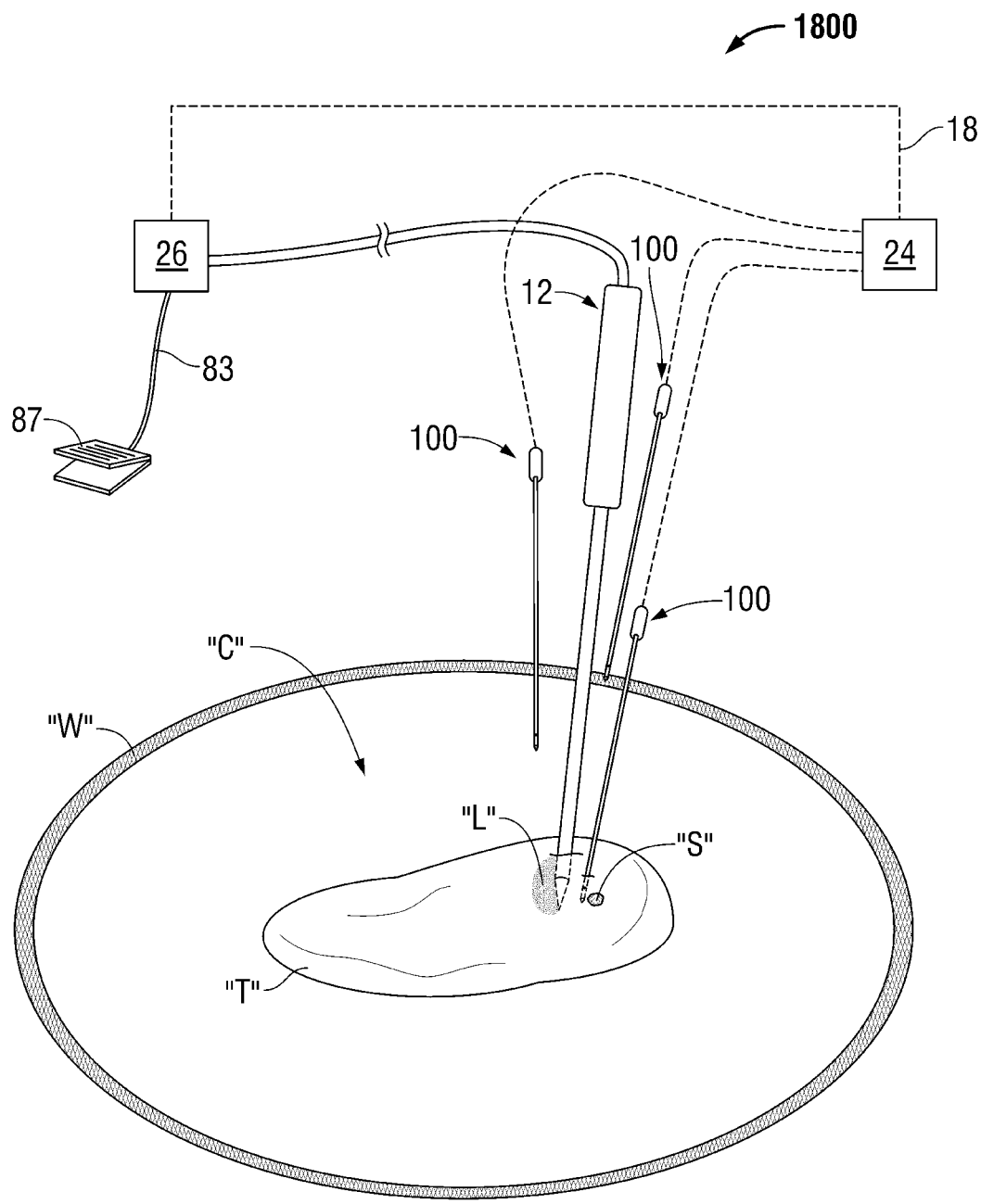
FIG. 18 is a schematic perspective view of an electrosurgical system according to an embodiment of the present disclosure.

FIG. 18 shows an electrosurgical system 1800 according to an embodiment of the present disclosure that includes an energy applicator or probe 12 operably coupled to an electrosurgical power generating source 26. In some embodiments, the probe 12 may be coupled in fluid communication with a coolant supply system (not shown).

Electrosurgical system 1800 (also referred to herein as a "microwave ablation control system") generally includes one or more microwave field-detecting needle assemblies 100 and a control unit 24 in operable communication with the one or more microwave field-detecting needle assemblies 100. Control unit 24 and the one or more microwave field-detecting needle assemblies 100 may utilize wired communication and/or wireless communication. Control unit 24 is similar to the control unit 28 shown in FIG. 4 and further description thereof is omitted in the interests of brevity. Electrosurgical system 1800 according to various embodiments may include a feedback loop 18 suitable for use in controlling an energy applicator or probe 12 based on one or more electrical signals transmitted by one or more microwave field-detecting needle assemblies 100. Feedback loop 18 may utilize a cable connection and/or a wireless connection, e.g., a radiofrequency or infrared link.

In some embodiments, the microwave ablation control system 1800 may adjust the ablation field radiating about at least a portion of the energy applicator 12 into tissue by adjusting one or more operating parameters associated with the electrosurgical power generating source 26 based on one or more electrical signals transmitted by one or more microwave field-detecting needle assemblies 100. In the embodiment illustrated in FIG. 18, the plurality of microwave field-detecting needle assemblies 100 in operable communication with the control unit 24 are operable coupled via the feedback loop 18 to the electrosurgical power generating source 26. Examples of operating parameters associated with the electrosurgical power generating source 26 include temperature, impedance, power, current, voltage, mode of operation, and duration of application of electromagnetic energy.

It is to be understood that, although one energy applicator 12 and three microwave field-detecting needle assemblies 100 are shown in FIG. 18, electrosurgical system embodiments may utilize single or multiple energy applicators (or applicator arrays) and one or more microwave field-detecting needle assemblies. The single or multiple energy applicators and the one or more microwave field-detecting needle assemblies may be arranged in any suitable configuration.

Electrosurgical power generating source 26 may be any generator suitable for use with electrosurgical devices, and may be configured to provide various frequencies of electromagnetic energy. In some embodiments, the electrosurgical power generating source 26 is configured to provide microwave energy at an operational frequency from about 300 MHz to about 10 GHz. In other embodiments, the electrosurgical power generating source 26 is configured to provide electrosurgical energy at an operational frequency from about 400 KHz to about 500 KHz.

In some embodiments, the electrosurgical power generating source 26 is configured or set to a predetermined setting. For example, electrosurgical power generating source 26 may be set to a predetermined temperature, such as a temperature that may be used for the treatment of pain (e.g., about 42° C. or about 80° C.), a predetermined waveform, a predetermined duty cycle, a predetermined time period or duration of activation, etc.

Figure 19:
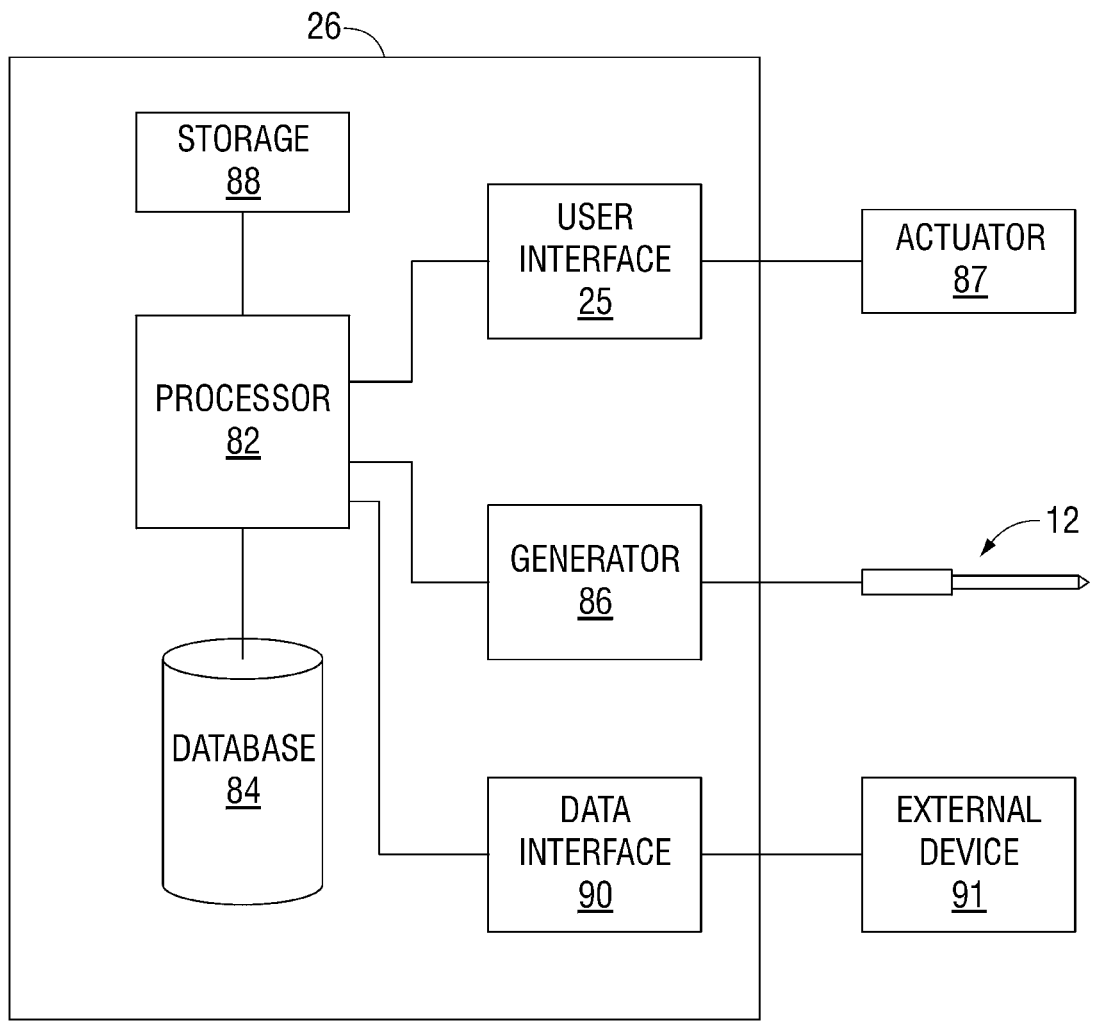
FIG. 19 is a block diagram of an embodiment of the electrosurgical power generating source of FIG. 18 in accordance with the present disclosure.

Electrosurgical power generating source 26 may include a user interface 25 (FIG. 19) in operable communication with a processor unit 82 (FIG. 19). Processor unit 82, which is described in more detail with respect to FIG. 19, may be any type of computing device, computational circuit, or any type of processor or processing circuit capable of executing a series of instructions that are stored in a memory. In an embodiment, a physician may input via the user interface 25 a selected power output, and the microwave ablation control system 1800 controls the probe 12 to automatically adjust the ablation volume by changing the operating frequency of the probe 12, e.g., based on at least one electrical signal transmitted by the one or more microwave field-detecting needle assemblies 100.

In an embodiment, a physician may input via the user interface 25 a selected power output, and the microwave ablation control system 1800 controls the ablation field radiating about at least a portion of the energy applicator 12 into tissue based on one or more electrical signals transmitted by one or more microwave field-detecting needle assemblies 100, e.g., by rotation of a energy applicator with a directional radiation pattern to avoid ablating sensitive structures, such as large vessels, healthy organs or vital membrane barriers and/or by controlling the electrosurgical power generating source 26 operatively associated with an energy applicator 12.

During microwave ablation using the microwave ablation control system 1800, one or more microwave field-detecting needle assemblies 100 may be inserted into tissue "T" and/or placed adjacent a sensitive structure "S", and/or one or more microwave field-detecting needle assemblies 100 may be inserted into the abdominal wall "W" and/or into the abdominal cavity "C". Probe 12 is inserted into tissue "T" and/or placed adjacent to a lesion "L". Ultrasound or computed tomography (CT) guidance may be used to accurately guide the probe 12 into the area of tissue to be treated. Probe 12 and one or more microwave field-detecting needle assemblies 100 may be placed percutaneously or surgically, e.g., using conventional surgical techniques by surgical staff. After the one or more microwave field-detecting needle assemblies 100 and the probe 12 are positioned, microwave energy is supplied to the probe 12.

A clinician may pre-determine the length of time that microwave energy is to be applied. Application duration may depend on many factors such as tumor size and location and whether the tumor was a secondary or primary cancer. The duration of microwave energy application using the probe 12 may depend on the progress of the heat distribution within the tissue area that is to be destroyed and/or the surrounding tissue. Treatment of certain tumors may involve probe repositioning during the ablation procedure, such as where the tumor is larger than the probe or has a shape that does not correspond with available probe geometry or radiation pattern.

FIG. 19 is a block diagram showing one embodiment of the electrosurgical power generating source 26 of FIG. 18. In an embodiment, the generator module 86 is configured to provide energy of about 915 MHz. Generator module 86 may additionally, or alternatively, be configured to provide energy of about 2450 MHz (2.45 GHz). The present disclosure contemplates embodiments wherein the generator module 86 is configured to generate a frequency other than about 915 MHz or about 2450 MHz, and embodiments wherein the generator module 86 is configured to generate variable frequency energy. Electrosurgical power generating source 26 includes a processor 82 that is operably coupled to the user interface 25. Processor 82 may include any type of computing device, computational circuit, or any type of processor or processing circuit capable of executing a series of instructions that are stored in a memory, e.g., storage device 88 or external device 91.

In some embodiments, storage device 88 is operably coupled to the processor 82, and may include random-access memory (RAM), read-only memory (ROM), and/or non-volatile memory (NV-RAM, Flash, and disc-based storage). Storage device 88 may include a set of program instructions executable on the processor 82 for executing a method for displaying and controlling ablation patterns in accordance with the present disclosure. Electrosurgical power generating source 26 may include a data interface 90 that is configured to provide a communications link to an external device 91. In some embodiments, the data interface 90 may be any of a USB interface, a memory card slot (e.g., SD slot), and/or a network interface (e.g., 100BaseT Ethernet interface or an 802.11 "Wi-Fi" interface.) External device 91 may be any of a USB device (e.g., a memory stick), a memory card (e.g., an SD card), and/or a network-connected device (e.g., computer or server).

Electrosurgical power generating source 26 may also include a database 84 that is configured to store and retrieve energy applicator data, e.g., parameters associated with one or energy applicators (e.g., 12 shown in FIGS. 18 and 19). Parameters stored in the database 84 in connection with an energy applicator, or energy applicator array, may include, but are not limited to, energy applicator (or applicator array) identifier, energy applicator (or applicator array) dimensions, a frequency, an ablation length, an ablation diameter, a temporal coefficient, a shape metric, and/or a frequency metric. In an embodiment, ablation pattern topology may be included in the database 84, e.g., a wireframe model of an applicator array and/or an ablation pattern associated therewith and/or an arrangement of microwave field-detecting needle assemblies for use in connection with one or more energy applicators.

Database 84 may also be maintained at least in part by data provided by the external device 91 via the data interface 90. For example without limitation, data associated with energy applicator 12 may be uploaded from an external device 91 to the database 84 via the data interface 90. Energy applicator data may additionally, or alternatively, be manipulated, e.g., added, modified, or deleted, in accordance with data and/or instructions stored on the external device 91. In an embodiment, the set of energy applicator data represented in the database 84 is automatically synchronized with corresponding data contained in the external device 91 in response to the external device 91 being coupled (e.g., physical coupling and/or logical coupling) to the data interface 90.

Processor 82 according to various embodiments is programmed to enable a user, via the user interface 25 and/or a display device (not shown), to view at least one ablation pattern and/or other data corresponding to an energy applicator or an applicator array. For example, a physician may determine that a substantially spherical ablation pattern is necessary. The physician may activate a "select ablation shape" mode of operation for electrosurgical power generating source 26, preview an energy applicator array by reviewing graphically and textually presented data, optionally, or alternatively, manipulate a graphic image by, for example, rotating the image, and select an energy applicator or an applicator array, based upon displayed parameters. The selected energy applicator(s) may then be electrically coupled to the electrosurgical power generating source 26 for use therewith.

Electrosurgical power generating source 26 may include an actuator 87. Actuator 87 may be any suitable actuator, e.g., a footswitch, a handswitch, an orally-activated switch (e.g., a bite-activated switch and/or a breath-actuated switch), and the like. Actuator 87 may be operably coupled to the processor 82 by a cable connection (e.g., 83 shown in FIG. 18) or a wireless connection, e.g., a radiofrequency or infrared link.

In an embodiment, a physician may input via the user interface 25 an applicator array parameter to cause the electrosurgical power generating source 26 to present one or more electromagnetic energy delivery devices corresponding thereto and/or one or more microwave field-detecting needle assemblies for use therewith. For example, a physician may require a 3.0 cm×3.0 cm×3.0 cm ablation pattern, and provide an input corresponding thereto. In response, the electrosurgical power generating source 26 may preview a corresponding subset of available electromagnetic energy delivery devices that match or correlate to the inputted parameter.

In an embodiment, a physician may input via the user interface 25 a selected power output, and the electrosurgical system 1800 controls the energy applicator 12 to adjust the ablation field radiating about at least a portion of the energy applicator 12 into tissue based on at least one electrical signal transmitted by the one or more microwave field-detecting needle assemblies.

Hereinafter, a method of manufacturing a needle assembly in accordance with the present disclosure is described with reference to FIG. 20, a method of manufacturing a microwave field-detecting needle assembly in accordance with the present disclosure is described with reference to FIG. 21, and a method of adjusting an ablation field radiating into tissue is described with reference to FIG. 22. It is to be understood that the steps of the methods provided herein may be performed in combination and in a different order than presented herein without departing from the scope of the disclosure.

Figure 20:
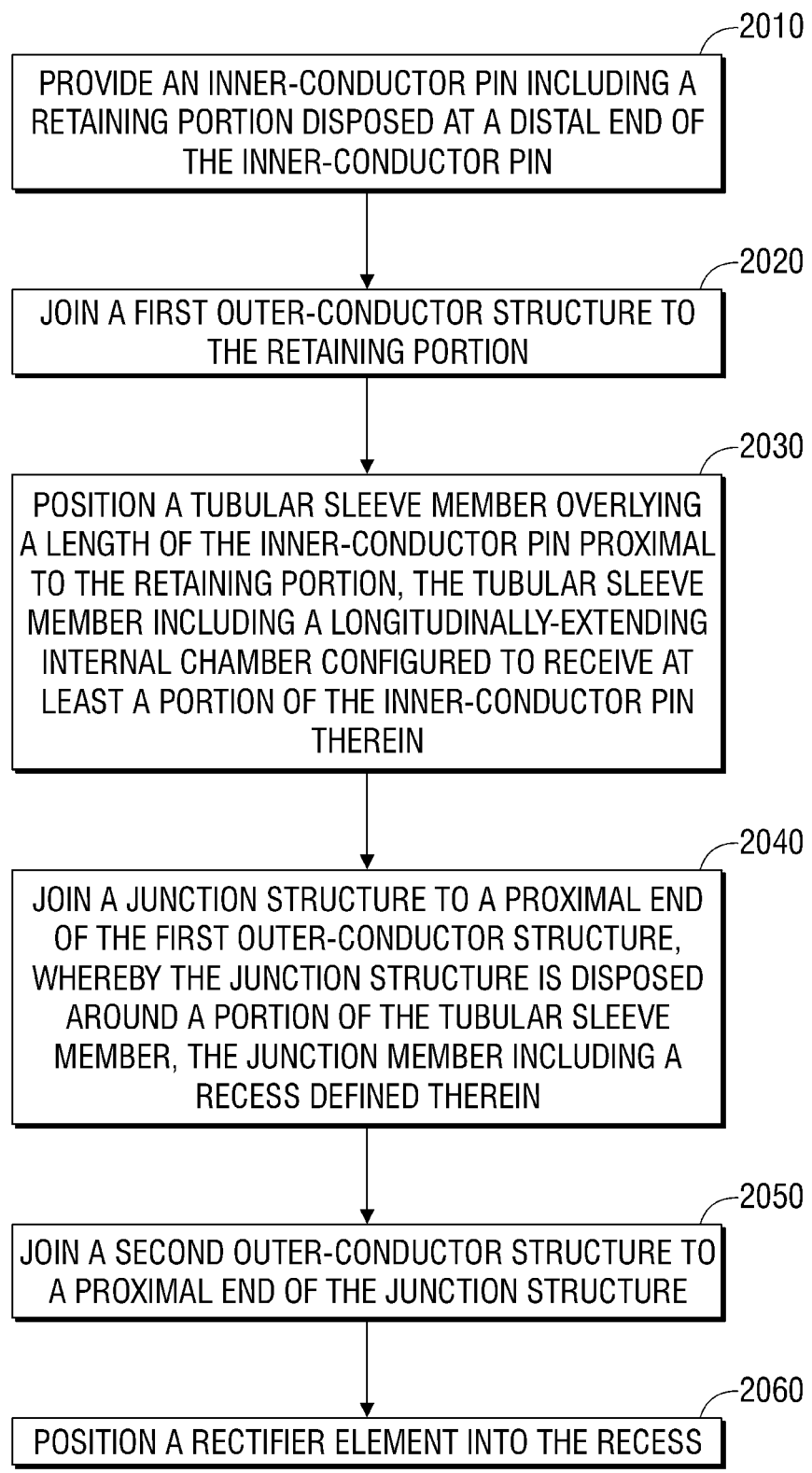
FIG. 20 is a flowchart illustrating a method of method of manufacturing a needle assembly according to an embodiment of the present disclosure.

FIG. 20 is a flowchart illustrating a method of manufacturing a needle assembly according to an embodiment of the present disclosure. In step 2010, an inner-conductor pin 20 is provided. A retaining portion 23 is disposed at a distal end 22 of the inner-conductor pin 20.

In step 2020, a first outer-conductor structure 30 is joined to the retaining portion 23.

In step 2030, a tubular sleeve member 40 is positioned overlying a length of the inner-conductor pin 20 proximal to the retaining portion 23. The tubular sleeve member 40 includes a longitudinally-extending internal chamber 45 configured to receive at least a portion of the inner-conductor pin 20 therein.

In step 2040, a junction structure 50 is joined to the proximal end 31 of the first outer-conductor structure 30, whereby the junction structure 50 is disposed around a portion of the tubular sleeve member 40. The junction structure 50 includes a recess 56 defined therein. The distal end 52 of the junction member 50 may be provided with a series of external threads configured to matingly engage with a series of internal threads disposed at the proximal end 31 of the first outer-conductor structure 30.

In step 2050, a second outer-conductor structure 60 is joined to the proximal end 51 of the junction structure 50. The proximal end 51 of the junction member 50 may be provided with a series of external threads configured to matingly engage with a series of internal threads disposed at the distal end 62 of the second outer-conductor structure 60.

In step 2060, a rectifier element 58 is positioned into the recess 56. In some embodiments, the rectifier element 58 includes a first terminal 59a and a second terminal 59b. In such cases, the first terminal 59a may be electrically coupled to the first outer-conductor structure 30 and the second terminal 59b may be electrically coupled to the second outer-conductor structure 60, e.g., by solder or other suitable electrical connection.

Figure 21:
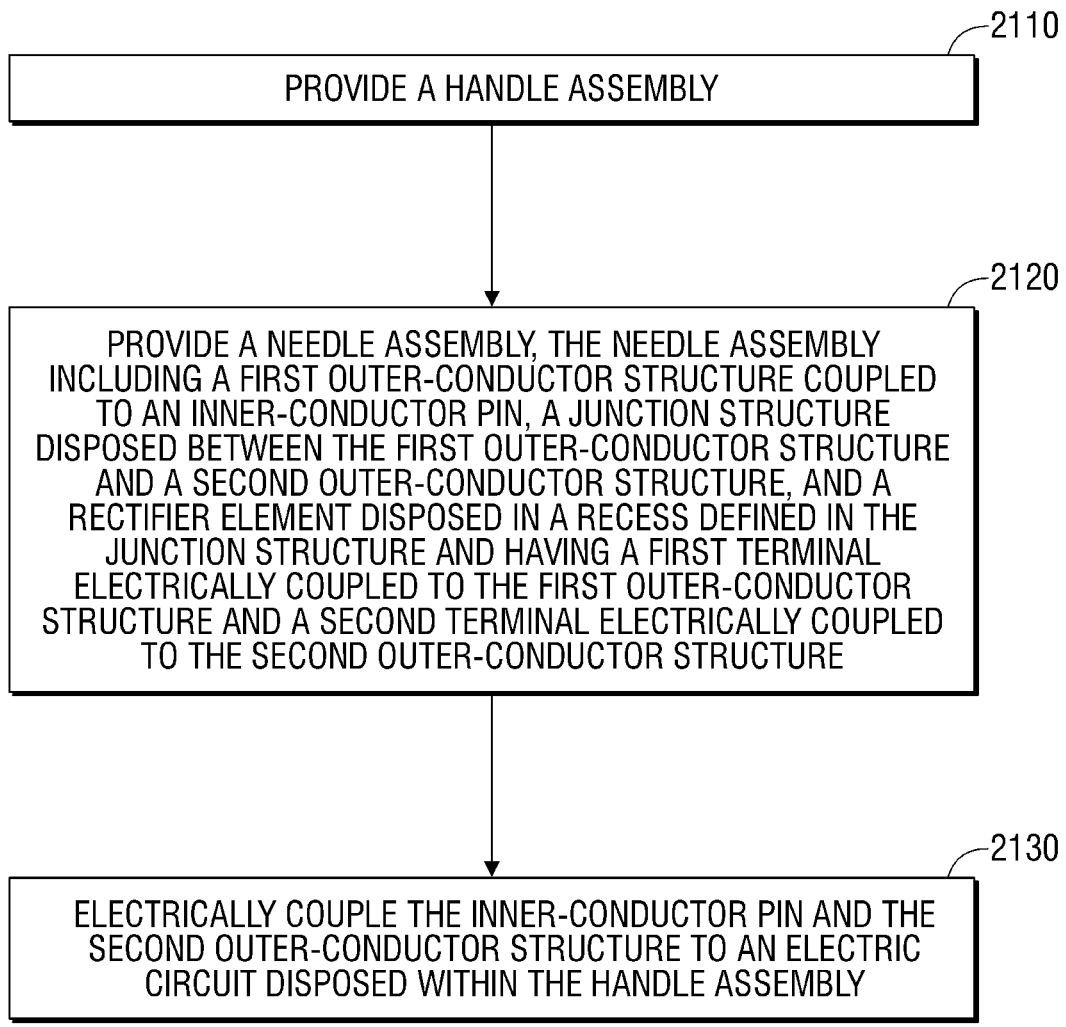
FIG. 21 is a flowchart illustrating a method of method of manufacturing a microwave field-detecting needle assembly according to an embodiment of the present disclosure.

FIG. 21 is a flowchart illustrating a method of manufacturing a microwave field-detecting needle assembly according to an embodiment of the present disclosure. In step 2110, a handle assembly 170 is provided. An electric circuit 300 is disposed within the handle assembly 170.

In step 2120, a needle assembly 110 is provided. The needle assembly 110 includes a first outer-conductor structure 30 coupled to an inner-conductor pin 20, a junction structure 50 disposed between the first outer-conductor structure 30 and a second outer-conductor structure 60, and a rectifier element 58 disposed in a recess 56 defined in the junction structure 50. A first terminal 59a of the rectifier element 58 is electrically coupled to the first outer-conductor structure 30, and a second terminal 59b is electrically coupled to the second outer-conductor structure 60.

In step 2130, the inner-conductor pin 20 and the second outer-conductor structure 60 are electrically coupled to an electric circuit 300 disposed within the handle assembly 170.

Figure 22:
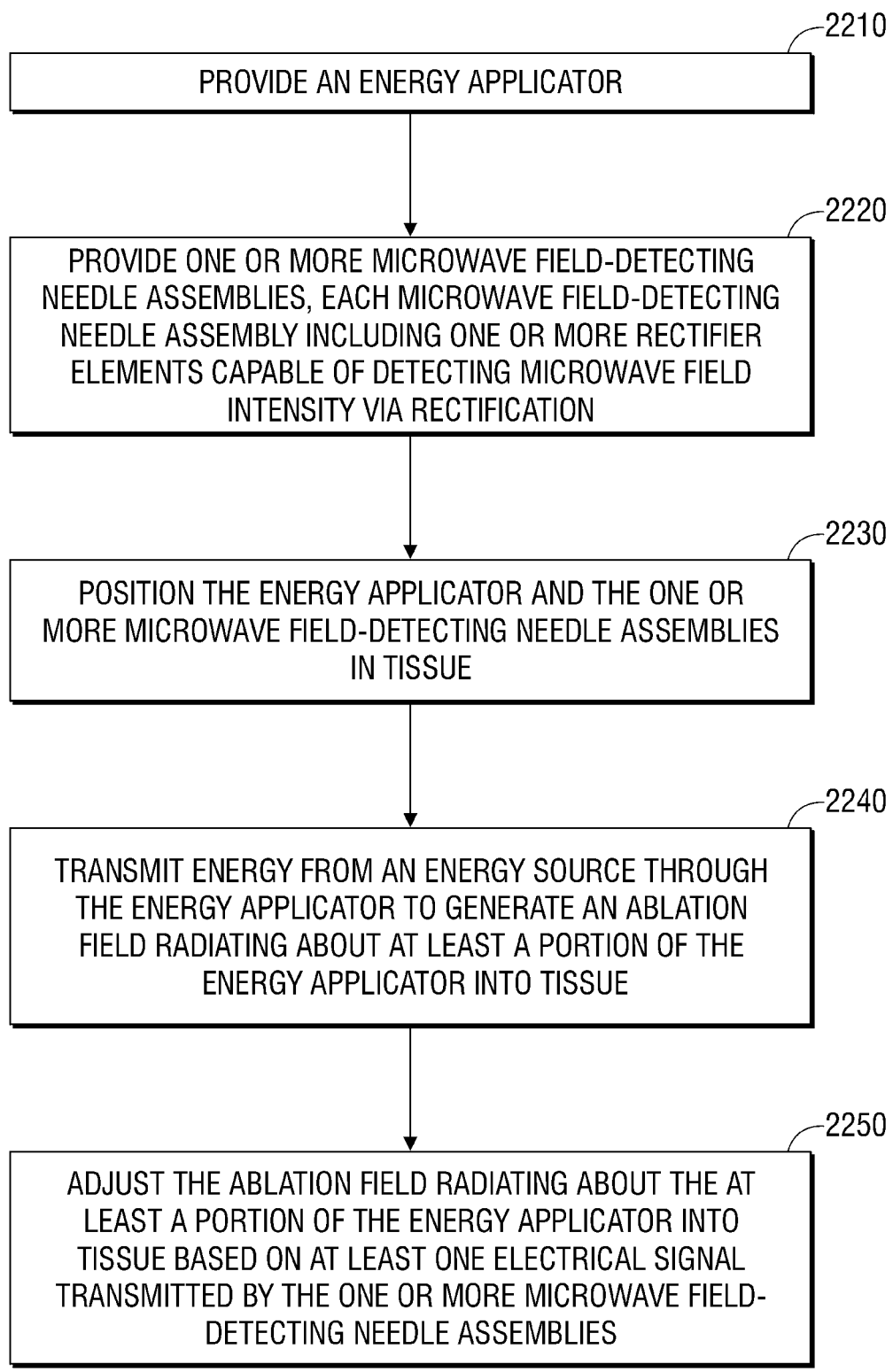
FIG. 22 is a flowchart illustrating a method of adjusting an ablation field radiating into tissue.

FIG. 22 is a flowchart illustrating a method of adjusting an ablation field radiating into tissue according to an embodiment of the present disclosure. In step 2210, an energy applicator 12 is provided. In step 2220, one or more microwave field-detecting needle assemblies 100 are provided. Each microwave field-detecting needle assembly 100 includes one or more rectifier elements 58 capable of detecting microwave field intensity via rectification.

In step 2230, the energy applicator 12 and the one or more microwave field-detecting needle assemblies 100 are positioned in tissue. The energy applicator 12 may be inserted directly into tissue, inserted through a lumen, e.g., a vein, needle, endoscope or catheter, placed into the body during surgery by a clinician, or positioned in the body by other suitable methods known in the art. The energy applicator 12 may be configured to operate with a directional radiation pattern. The one or more microwave field-detecting needle assemblies 100 may be positioned in material, e.g., tissue, by any suitable method and arranged in any configuration (e.g., configuration shown in FIG. 18).

In step 2240, energy is transmitted from an energy source 26 through the energy applicator 12 to generate an ablation field radiating about at least a portion of the energy applicator 12 into tissue. The energy source 26 may be any suitable electrosurgical generator for generating an output signal. In some embodiments, the energy source 26 is a microwave energy source, and may be configured to provide microwave energy at an operational frequency from about 300 MHz to about 10 GHz.

In step 2250, the ablation field radiating about at least the portion of the energy applicator 12 into tissue is adjusted based on at least one electrical signal transmitted by the one or more microwave field-detecting needle assemblies 100. In some embodiments, adjusting the ablation field radiating about at least the portion of the energy applicator 12 into tissue, in step 2250, may include adjusting at least one operating parameter associated with the energy source 26 based on the at least one electrical signal transmitted by the one or more microwave field-detecting needle assemblies 100. Examples of operating parameters associated with the energy source 26 include temperature, impedance, power, current, voltage, mode of operation, and duration of application of electromagnetic energy.

According to various embodiments of the present disclosure, the above-described microwave field-detecting needle assembly enables physicians to detect field intensity in proximity to an energy-delivery device. The presently-disclosed microwave field-detecting needle assembly embodiments may allow the physician to determine if a microwave field is strong enough for the intended purpose or to achieve a desired surgical outcome.

The presently-disclosed microwave field-detecting needle assembly embodiments may be suitable for utilization in minimally invasive procedures, e.g., endoscopic and laparoscopic surgical procedures. The above-described microwave field-detecting needle assembly embodiments may be suitable for utilization in open surgical applications.

Various embodiments of the presently-disclosed microwave field-detecting needle assembly embodiments may allow the physician to determine when a microwave ablation probe is inserted to a proper depth within tissue, e.g., to reach the location of the ablation site and/or to avoid unintended field exposure. Various embodiments of the presently-disclosed microwave field-detecting needle assembly are adapted to be coupled in communication with a stand-alone control unit.

Electrosurgical systems including one or more microwave field-detecting needle assemblies according to embodiments of the present disclosure may protect sensitive structures, ensure expected field pattern and/or protect the abdominal wall from stray microwave fields.

The above-described microwave field-detecting needle assemblies may be used to detect microwave field intensity emitted by an energy applicator, and an electrical signal transmitted from the presently-disclosed microwave field-detecting needle assemblies may be used to control the positioning of an electrosurgical device (e.g., rotation of a energy applicator with a directional radiation pattern to avoid ablating sensitive structures, such as large vessels, healthy organs or vital membrane barriers), and/or control an electrosurgical power generating source operatively associated with an energy applicator.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of adjusting an ablation field radiating into tissue, the method comprising:
   positioning an energy applicator into tissue;
   positioning at least one microwave field-detecting needle assembly in tissue independently from the energy applicator, the at least one microwave field-detecting needle assembly including at least one rectifier element capable of detecting microwave field intensity via rectification;
   transmitting energy from an energy source through the energy applicator to generate an ablation field radiating about at least a portion of the energy applicator into tissue; and
   adjusting the ablation field radiating about the at least a portion of the energy applicator into tissue based on at least one electrical signal transmitted by the at least one microwave field-detecting needle assembly.

2. The method of adjusting an ablation field radiating into tissue of claim 1, wherein the energy source is an electrosurgical power generating source.

3. The method of adjusting an ablation field radiating into tissue of claim 2, wherein adjusting the ablation field radiating about the at least a portion of the energy applicator into tissue includes:
   adjusting at least one operating parameter associated with the electrosurgical power generating source based on the at least one electrical signal transmitted by the at least one microwave field-detecting needle assembly.

4. The method of adjusting an ablation field radiating into tissue of claim 3, wherein the at least one operating parameter associated with the electrosurgical power generating source is selected from the group consisting of temperature, impedance, power, current, voltage, mode of operation, and duration of application of electromagnetic energy.

5. A method of adjusting an ablation field radiating into tissue, the method comprising:
   positioning an energy applicator operably coupled to an energy source into tissue;
   positioning at least one microwave field-detecting needle assembly into tissue independently from the energy applicator, the at least one microwave field-detecting needle assembly including at least one rectifier element capable of detecting microwave field intensity via rectification;
   positioning the energy applicator and the at least one microwave field-detecting needle assembly in tissue;
   transmitting energy from an energy source through the energy applicator to generate an ablation field radiating about at least a portion of the energy applicator into tissue; and
   adjusting the ablation field radiating about the at least a portion of the energy applicator into tissue by adjusting at least one operating parameter associated with the energy source based on at least one electrical signal transmitted by the at least one microwave field-detecting needle assembly.

6. The method of adjusting an ablation field radiating into tissue of claim 5, wherein the at least one operating parameter associated with the energy source is selected from the group consisting of temperature, impedance, power, current, voltage, mode of operation, and duration of application of electromagnetic energy.

* * * * *